United States Patent [19]

Berg et al.

[11] Patent Number: 4,841,962

[45] Date of Patent: Jun. 27, 1989

[54] COLLAGEN MATRIX/POLYMER FILM COMPOSITE DRESSING

[76] Inventors: Richard A. Berg, R.D. #1, Box 148, Lambertville, N.J. 08530; Frederick H. Silver, R.D. #1, Box 1128, Bangor, Pa. 18013; James M. Pachence, 7 Chopin La., Lawrenceville, N.J. 08648; John D'Antonio, 11 Lovers La., Princeton, N.J. 08540

[21] Appl. No.: 95,779

[22] Filed: Sep. 11, 1987

Related U.S. Application Data

[63] Continuation-in-part of Ser. No. 875,827, Jun. 18, 1986, which is a continuation-in-part of Ser. No. 843,828, Mar. 26, 1986, Pat. No. 4,703,108, which is a continuation of Ser. No. 593,733, Mar. 27, 1984, abandoned.

[51] Int. Cl.[4] .............................................. A61L 15/00
[52] U.S. Cl. ............................. 128/156; 128/DIG. 8; 530/356
[58] Field of Search ................. 530/356; 128/DIG. 8; 524/17, 21; 527/201

[56] References Cited

U.S. PATENT DOCUMENTS 4,060,081 11/1977 Yannas et al. ......................... 623/66
4,703,108 10/1987 Silver et al. .......................... 530/356

*Primary Examiner*—John Kight
*Assistant Examiner*—Nathan M. Nutter

[57] ABSTRACT

A wound dressing comprising a crosslinked collagen matrix; a bioabsorbable adhesive coated on one surface of the collagen matrix; a multilayer polymer film imparting pre-selected moisture vapor and gas transmissivity to the dressing, secured to the opposite surface of the collagen matrix; and an adhesive securing the collagen matrix to the polymer film.

8 Claims, 2 Drawing Sheets

COLLAGEN MATRIX/POLYMER FILM COMPOSITE DRESSING

CROSS-REFERENCE TO RELATED APPLICATIONS

This application is a continuation-in-part of copending application Ser. No. 875,827 filed June 18, 1986; which was a continuation-in-part of application Ser. No. 843,828 filed Mar. 26, 1986 and now U.S. Pat. No. 4,703,108; which application was in turn a continuation of application Ser. No. 593,733 filed Mar. 27, 1984, now abandoned.

TECHNICAL FIELD

This invention relates to a wound dressing and, more particularly, to a combination collagen/synthetic film wound dressing.

BACKGROUND OF THE INVENTION

The design of an effective wound dressing depends on many factors, including the method of delivery, adherence to the wound, maintenance of a moist environment, minimization of pooling of wound fluids between the tissue and the dressing, prevention of secondary bacterial infection, protection against reinjury, adequate transmission of moisture vapor from the wound bed, no reinjury upon removal of the wound dressing and flexibility of the dressing itself.

Wound dressings prepared from various forms of collagen are known, including collagen sponges, films, powders and enzyme-solubilized gels. We have described these dressings, as well as other medical applications of collagen, in a recent review. Pachence J. M., Berg R. A. and Silver F. H., "Collagen: Its Place in the Medical Device Industry", Med. Device & Diag. Ind., 9: 49–55, 1987. Collagen sponges used as wound dressings are described, for example, in Cioca U.S. Pat. No. 4,412,947 granted Nov. 1, 1983, Berg et al U.S. Pat. No. 4,320,201 granted Mar. 16, 1982, and Artandl, U.S Pat. No. 3,157,524. Non crosslinked or lightly crosslinked collagen sponges fail to provide adequate barriers against bacterial contamination or wound reinjury and resorb too rapidly.

In an effort to eliminate these problems, a dressing has been developed, comprising a collagen compressed foam film laminated, without the use of adhesive, to a thin layer of an inert polymer, as described in McKnight et al., U.S. Pat. No. 3,800,792 granted Apr. 2, 1974. However, collagen films, although providing an adequate barrier against bacterial contamination or wound reinjury, have poor fluid absorption properties and enhance the pooling of wound fluids.

Accordingly, it is among the objects of the present invention to provide an improved collagen matrix/polymer film wound dressing having pre-selected moisture and gas transmissivity characteristics, which greatly control and enhance fluid absorption properties while simultaneously accelerating wound heal time and quality. Additionally, the dressing prohibits maceration and the development of anaerobic bacteria.

SUMMARY OF THE INVENTION

In accordance with this invention, a wound dressing is provided, comprising a crosslinked collagen matrix; a bioabsorbable adhesive coated on the surface of the collagen matrix which is placed in contact with the wound bed; a multilayer polymer film providing pre-selected moisture vapor and gas transmissivity, which is secured to the opposite side of the collagen matrix, the layer of the film remote from the collagen matrix being strippable from the film after a predetermined period of time to provide increased moisture vapor transmission between the wound bed and the atmosphere, and an adhesive securing the collagen matrix to the polymer film. Composite wound dressings of this type absorb up to forty times their weight in liquid, while remaining firmly secured to the wound. The wound dressing hereof has the further advantage of controlling moisture and gas transmission through the use of films having varying degrees of microporosity and occlusivity at selected stages in the wound healing process while providing a barrier against bacterial infection and reinjury of the wound. This dressing is particularly useful for partial or full thickness wounds since it is important that such wounds are protected against moisture loss, bacterial contamination, reinjury, and skin maceration.

A particularly significant advantage of the dressing of the present invention is the ability to remove the outer more occlusive polymer film layer after a period of time, determined by the stage of healing and still retain a microporous semipermeable film (the inner polymer film layer). This promotes wound healing while preventing maceration and exogenous bacterial contamination.

A further advantage of the dressing of the invention is the ability to provide either a fully occluded barrier or a semi-occlusive dressing through the use of more than one layer of film.

A further advantage of the wound dressing of the present invention is the ability to use either Type I or Type III collagen in the collagen matrix. Type I collagen in particular is a material that is readily available, has a high degree of biocompatability, absorbs many times its own weight in liquid, is minimally antigenic, and provides a natural attachment site for cells involved in the wound healing process.

Another advantage of the present invention is the ability to have agents incorporated into the collagen matrix and subsequently delivered to the wound site which affect cell growth, such as collagen types IV and V, fibronectin, laminin, hyaluronic acid, and proteoglycans. Similarly, pharmacologically active agents such as epidermal growth factor, platelet derived growth factor, transforming growth factor beta, angiogenesis factor, antibiotics, antifungals, spermicidals, hormones, enzymes, and/or enzyme inhibitors can also be incorporated into the collagen matrix.

BRIEF DESCRIPTION OF THE DRAWING

In the accompanying drawing, illustrating preferred embodiments of the wound dressing of the invention.

DETAILED DESCRIPTION

Figure 1:
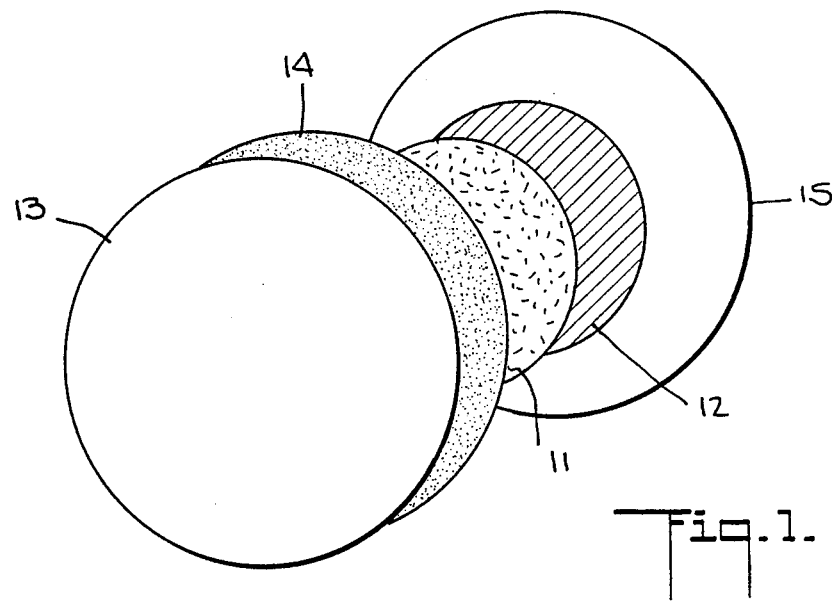
FIG. 1 is a diagrammatic exploded perspective view of one embodiment of the invention.
Figure 2:
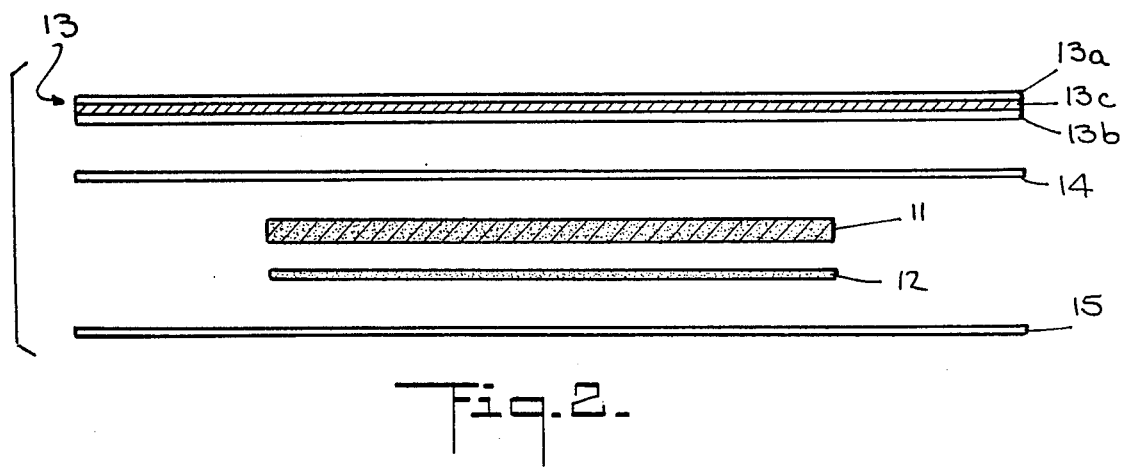
FIG. 2 is a schematic cross-section of FIG. 1, with the various layers of the composite assembly shown in spaced relation for ease of explanation.
Figure 3:
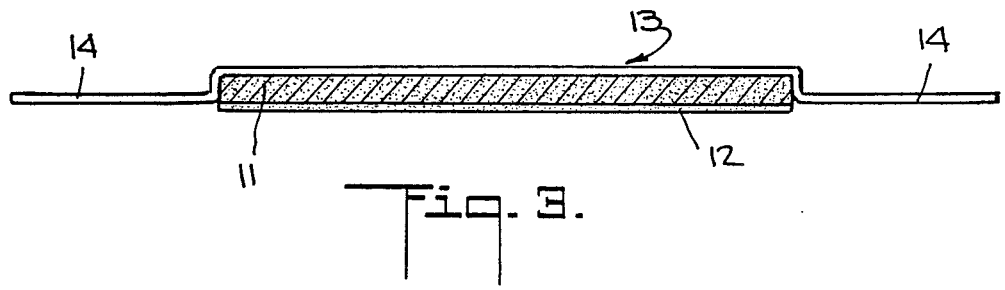
FIG. 3 is a cross sectional view of the embodiment of FIGS. 1 and 2 as placed on a wound site, with the protective release paper removed.

As illustrated in FIGS. 1, 2 and 3, the wound dressing of the present invention comprises a crosslinked collagen matrix 11, a bioabsorbable adhesive 12 coated on the surface of the matrix to be placed in contact with the wound bed, a multilayer polymer film 13 adjacent the opposite surface of the matrix, and an adhesive 14 securing the collagen matrix to the polymer film. Preferably, the collagen matrix is made from Type I or Type III collagen. The crosslinked collagen matrix may have an average pore size of about 50 to 350 microns, preferably $100 \pm 50$ microns, with the collagen comprising up to about 30%, preferably about 2 to 30%, by volume of the matrix.

The collagen is in the form of a crosslinked material having a molecular weight of about $1 \times 10^6$ to $50 \times 10^6$ or more, where the molecular weight between adjacent crosslinks is about 1,000 to 100,000. The collagen matrix is in the form of a network of fine fibers having thicknesses varying from about 5 to 40 microns, preferably about 10 microns. The fibers define surface and interior pores connected by internal channels, the average pore size being about 50 to 350 microns, preferably $100 \pm 50$ microns, which is sufficiently open as to stimulate cellular ingrowth therethrough. The matrix is sufficiently stiff and non-compressible as to fill and protect a wound. Desirably, the matrix has a stiffness of from about $10^3$ to $10^5$ Newtons/m$^2$, preferably about $10^4$.

The collagen matrix employed in the present invention absorbs many times its weight in liquid. The amount of liquid retained by the collagen matrix is a function of the number of crosslinks (defined as "crosslink density"), and is calculated as the ratio of the volume of water absorbed per unit volume of collagen based matrix (known as the "swelling ratio"). The value of the swelling ratio for the collagen matrix used in the present invention is between 2.5 and 20, preferably between 10 and 20.

The collagen matrix is suitably prepared by dispersing Type I or Type III collagen in an appropriate solvent or diluent, then freezing the matrix as by lyophilization. The collagen matrix may be cross linked employing biologically inert, non-toxic crosslinking agents. More particularly, the collagen matrix may be prepared employing the techniques described, for example, in parent U.S. patent applications Ser. Nos. 593,733; 843,828; and 875,827.

Other agents may additionally be incorporated in the collagen matrix. Macromolecules such as hyaluronic acid or fibronectin (see "Fibroblast Growth on a Porous Collagen Sponge Containing Hyaluronic Acid or Fibronectin", Doillon, C. J., Silver, F. H. and Berg, R. A., Biomaterials 8:195–200), collagen types II, IV or V, laminin, and proteoglycans will affect cell growth when incorporated into the collagen matrix. Thus, when the collagen matrix is prepared as described above, the above mentioned macromolecules may be added to the collagen/organic acid dispersion, prior to formation of the crosslinked collagen matrix, in amounts of about 0.01 to 2.0% by volume of the dispersion.

Pharmacologically active agents such as platelet-derived growth factor (see Sato, G. H., Ross, R. eds. Hormones and Cell Culture, Books A and B, New York, Cold Spring Harbor), epidermal growth factor, transforming growth factor beta, (see Raghaw, R., Postlethwaite, A. E., Keski-Oja J., Moses, H. L., and Kang, A. H. (1987) 79:1285–1288), angeogenesis factor, topical antibiotics such as gentamycin, tetracycline, erythromycin, neomycin and others known to those of skill in the art, antifungal agents, spermicidal agents, hormones, enzymes, or enzyme inhibitors can also be incorporated in the collagen matrix and subsequently delivered to the tissue. The above mentioned agents are added to the collagen dispersion, prior to formation of the crosslinked collagen matrix, in amounts varying, for example, from 10 ng/ml to 10 g/ml for the growth factors, and 0.01 mg/ml to 10 mg/ml for hormones, enzymes and enzyme inhibitors. The chemical crosslinking and the pore size of the collagen matrix are altered in order to alter the delivery dose of these agents from the collagen matrix, so that 90% of the agent is delivered from the matrix in from 1 to 72 hours.

The bioabsorbable adhesive 12 is placed on the surface of the collagen matrix which is to come in contact with the subcutaneous tissue or wound bed. The bioabsorbable adhesive used may be selected from polyisobutylenes (e.g. Visanex -LLMH from Exxon) containing hydrophils such as carboxymethylcellulose (e.g. 7MXFCMC from Hercules Corp.), starch graft copolymers (e.g. Water Lock Products from Grain Processing Corpn.), pectins (e.g. USP 100 from Hercules Corpn.), gelatins (e.g. Food Grade Gelatins from Hercules Corpn.), and/or tackifiers such as resin esters (e.g. Piccotac\from Hercules Corp. and Piccolyte\- Hercules S115) or hydrocarbons including aromatics, aliphatics and terpenes; and/or plasticizers such as mineral oil; acrylic emulsions; polyvinyl ethyl ethers with hydrogenated resin esters; materials made from natural rubber latex; collagen adhesives containing tackifiers such as resin esters (Piccotac, Piccolyte) or hydrocarbons; tissue absorbable adhesives made from polyglycolic acid, polylactic acid, and polyhydroxybutyrate; and water-based urethane emulsions. Of these bioabsorbable adhesives polyisobutylenes are preferred, although polyacrylamides, urethane copolymers or polyvinylacetate may be used.

The bioabsorbable adhesive 12 is coated on the surface of the collagen matrix 11 by any known technique which will leave the collagen matrix intact, such as spray drying, ultrasonic spraying, co-casting the adhesive with the collagen dispersion, transfer coating, extrusion, gravure coating or knife over roll coating or any related process. Preferably, the bioabsorbable adhesive is placed on the collagen matrix by spray drying.

The multilayer polymer film 13 is secured to the collagen matrix 11 on the surface opposite adhesive coating 12. As illustrated in FIG. 3 of the drawing, the multilayer polymer film comprises at least two layers 13a, 13b. By modifying the materials constituting layers 13a, 13b, the moisture and gas transmissivity characteristics of the composite multilayer film are predetermined as may be desired. It should be understood that additional polymer layers can be added to further control the liquid and gas transmissivity of the composite membrane.

In particular, the gas and moisture transmission of the multilayer film is pre-selected depending upon the type of wound to be treated and modified by removing the outermost layer in a tear away fashion to offer the wound bed a combination of optimum occlusivity and moisture vapor transmission characteristics.

Examples of polymer film composites providing for these varied transmissivities include: butyl acrylate, microporous polyether polyurethane/microporous polyether polyurethane films having a thickness of 2 ml; and Teflon/microporous polyester polyurethane films.

In one preferred two layer film embodiment, the outer layer 13a (that remote from the collagen matrix) is desirably so chosen as to permit about 0 to 500 g/cm$^2$ per 24 hour period moisture transmission (an ASTM No. E96-BW, the ASTM value is measured as disclosed in D'Antonio, U.S. Pat. No. 4,632,860) and an oxygen permeability of about 500 to 6000 cm$^3$-m$^2$-Atmos-24 h (as measured by the Davenport Method). Polymers suitable for use in such layer include tetrafluoroethylene fluorocarbon resins (Teflon); microporous polyether polyurethanes; polyester polyurethanes (e.g. Normed Product line series KM 1351-00 through KM1358 from Semex Medical); acrylics such as butyl acrylate, polyvinyl acrylates; microporous polyvinyl chlorides; polyolefins; Mylar\a polyester film from DuPont; cellulose acetate (e.g. cellulose diacetate from Hutchison and Miller Sales Co.); polydifluoroethylene (Saran\Dow Corning); ethylene vinyl acetate; ionomeric films such as Surlyn, from DuPont; Neoprene\(chloroprene from DuPont); Hycar\ (styrene butadiene which includes polyacrylics, latexes and nitreils all from B.F. Goodrich Chemical Co.); Nitrile (DuPont); Butyl (Exxon), Viton (vinylidene fluoride hexafluoropropylene from DuPont), C-Flex\(styrene ethylenebutylene styrene block copolymer from Concept Polymer Technologies, Inc.), silicone latex (Dow Corning); EPT (ethylenepropylene turpolymer known as Nordell EPT from DuPont); EPDM (ethylenepropylene dimonomer known as Nordell EPDM from DuPont); and biodegradable urethanes (e.g. from Tyndale Plains Hunter Ltd.) Of these polymers, composites of butylacrylate/microporous polyether polyurethane layers of up to 8 ml thickness are preferred.

The inner polymer layer 13b is secured to the outer polymer layer 13a by a pressure sensitive medical grade adhesive such as butyl acrylate 13c (FIG. 2).

The second layer 13b (that closest to the collagen matrix) in such a preferred embodiment is desirably so chosen as to permit about 500 to 5000 gm/cm$^2$ per 24 hour period moisture transmission and an oxygen permeability of about 6000 to 20,000 cm$^3$-m$^2$-Atmos-24 h (as measured by the Davenport Method). Polymers suitable for use in such layer include tetrafluoroethylene fluorocarbon resins (Teflon); microporous polyether polyurethanes; polyester polyurethanes (e.g. Normed product line series KM-1351-00 through KM-1358 from Semex Medical); acrylics such as butyl acrylate, polyvinyl acrylates; microporous polyvinyl chlorides; polyolefins; Mylar—a polyester film from DuPont; cellulose acetate (e.g. cellulose diacetate from Hutchison and Miller Sales Co.); polydifluoroethylene (Saran\ from Dow Corning), ethylene vinyl acetate, ionomeric films such as Surlyn\ from DuPont, Neoprene (chloroprene from DuPont), Hycar\ (styrene butadiene which includes polyacrylics, latexes and nitriles all from B.F. Goodrich Chemical Co.), Nitrile (Du Pont), Butyl (Exxon), Viton\ vinylidene fluoride hexafluoropropylene from DuPont, C-Flex\ styrene ethylene butylene styrene block copolymer from concept Polymer Technologies, Inc.; silicone latex (Dow Corning); EPT (ethylenepropyleneturpolymer—Nordell EPT from DuPont); EPDM ethylenepropylene dimonomer— Nordell EPDM from DuPont; and biodegradable urethanes (from Tyndale Plains Hunter Ltd.).

The multilayer polymer film 13 is secured to the collagen matrix 11 by a standard medical grade adhesive 14 such as a microporous acrylate adhesive (e.g. Model TT 5022-00 from Semex Medical).

As illustrated in FIGS. 1 and 2, the wound dressing of the present invention further comprises a release layer 15 secured to the bioabsorbable adhesive 14 on the surface opposite that of the collagen matrix 11. Materials suitable for the release layer include polysiloxanes (e.g. polydimethylsiloxane -SCK, Silicone Coated Kraft FDA approved from James River Paper Co.), and carbamates (such as from Rohm and Haas).

Figure 4:
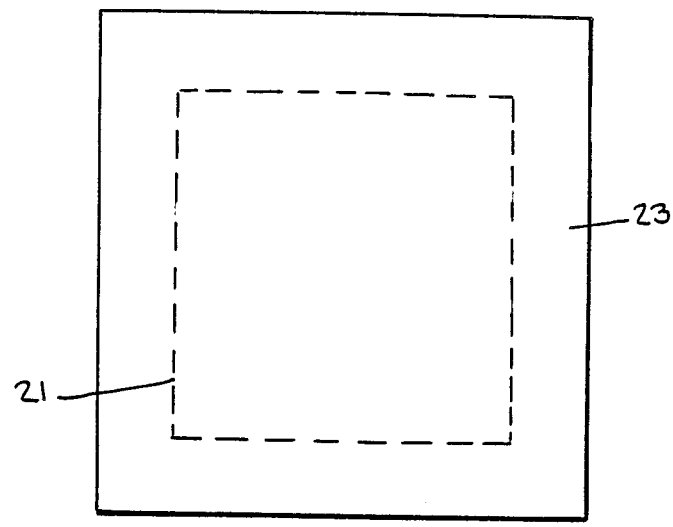
FIG. 4 is a plan view of an additional, rectangular embodiment of the invention.
Figure 5:
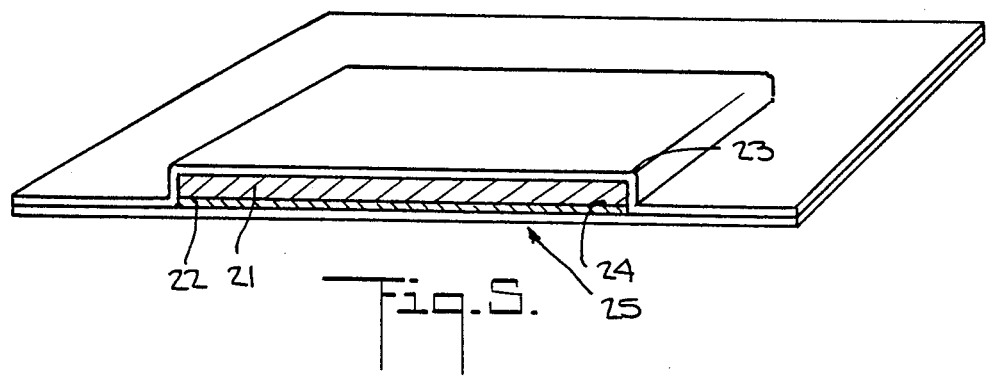
FIG. 5 is a schematic cross section of the wound dressing of FIG. 4.

In the further embodiment illustrated in FIGS. 4 and 5, the multilayer polymer film 23 secured to the collagen matrix 21 may extend beyond the boundary of the collagen matrix, thereby ensuring that the wound dressing is secured to the wound site.

Figure 6:
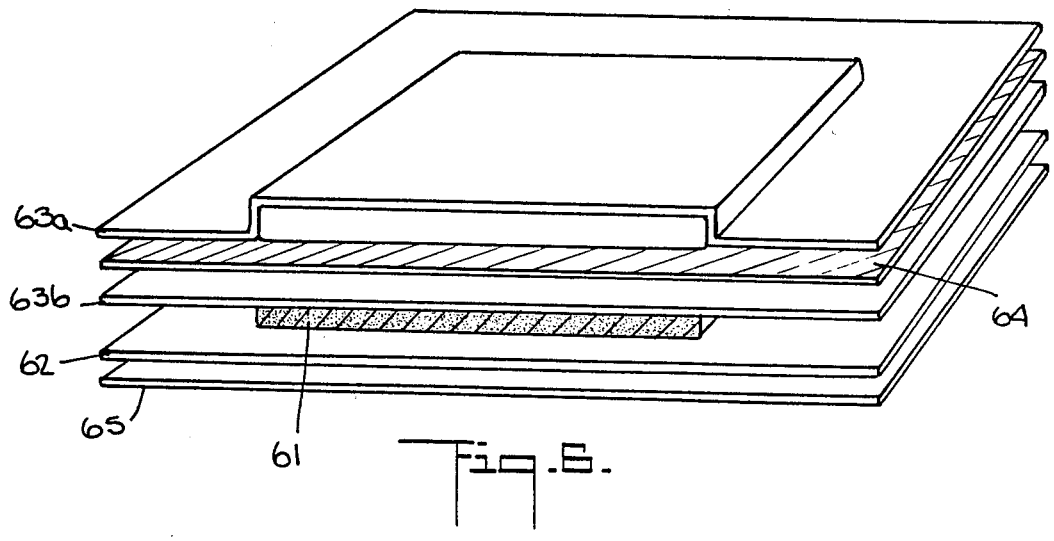
FIG. 6 is a cross sectional view of a further embodiment of the invention.

A further embodiment of the invention is illustrated in FIG. 6. In this product, the multilayer polymer film is so chosen that the outer layer 63a is removed from the wound dressing after a limited period of time to promote further wound healing. In the early stages of wound healing relative occlusivity promotes new cell growth. When the wound is approximately 50% healed, the outer layer 63a is removed, and the remaining semipermeable film 63b provides the wound bed with increased moisture vapor transmission e.g. if 63b permits 5000 g/cm$^2$ moisture vapor transmission and 63a permits only 500 g/cm$^2$ moisture vapor transmission, only 500 g/cm$^2$ will pass through the multilayer film; however, after stripping 63a the remaining film will transmit increased moisture vapor, viz. 5000 g/cm$^2$. This promotes wound healing at the later stage of the wound healing process while preventing maceration and exogenous bacterial contamination. The following examples illustrate particularly preferred embodiments of the wound dressing of the present invention:

EXAMPLE 1

A composite wound dressing of the type illustrated in FIG. 6 was prepared as follows:

A. The Occlusive Outer Polymer Film Layer

An acrylate basecoat was prepared from Reichold 2671 acrylic copolymer of styrene and butyl acrylate latex in water (40% dry weight) (obtained from Reichold Co. of Dover, Del.) 10 parts dry weight of copolymer (250 parts wet weight) were blended with 1.5 parts wet weight of Unithick thickener (obtained form Union Color and Chemical Co., of Morgantown, N.C.) for 2 minutes at 72° F.) 0.5 parts NH$^4$ OH (ammonium hydroxide) were added to raise the pH to approximately 7.0. After stirring for 2 minutes at 72° F., the butyl acrylate emulsion was cast onto polydimethylsiloxane (SCK—Silicone Coated Kraft, FDA approved from James River Paper Co.) release paper and oven-dried by a transfer coating process. This layer had a thickness of 1 ml.

A microporous polyurethane topcoat was prepared from polyether urethane TC 201 (obtained form Mill Master Onyx of Lyndhurst, N.J.) provided in 35% total solids solution in a 1:1 blend of N, N-dimethyl formamide (DMF) and toluene. 100 parts dry weight of polyurethane was blended with 500 parts dry weight of 325 mesh sodium chloride (NaCl) TFC 325 (obtained from Morton Salt Division of Morton Thiokol, Inc. of Chicago, ILL.) for 10 minutes at 72° F. Sufficient toluene was added to wet out the salt and adjust the viscosity of the topcoat to 5000 cps. The polyurethane topcoat was then cast onto the butylacrylate base by a transfer coating process. This film was then subjected to a high pressure water scour at 212° F. The release paper was removed resulting in a polymer film layer 63a which was 2 mm thick having a base stratum of butyl acrylate and a top stratum of microporous polyether polyurethane.

B. The Adhesive Layer

The second layer 64 of the wound dressing comprised of a pressure sensitive butyl acrylate adhesive approximately 1 mm thick was secured to the polymer layer 63a formed in (A) in such a manner as to border the periphery of the polymer layer.

C. The Inner Polymer Layer

The inner polymer layer 63b was the microporous polyether polyurethane described in Example 1 (A). The inner polymer layer 63b used had a high rate of moisture vapor (e.g. at least 2000 grams per square meter per 24 hour period). This microporous polyether polyurethane 63b was secured to the polymer layer 63a by the adhesive 64.

D. The Bioabsorbable Adhesive-Collagen Matrix Layer

The fourth layer is comprised of a bioabsorbable adhesive (hydrocolloid adhesive) 64 having a collagen matrix 61 secured to the center of the adhesive layer.

The bioabsorbable adhesive is Visanex-LLMH from Exxon (polyisobutylene) additionally containing the hydrophils carboxymethylcellulose, pectin and gelatin having Piccotec a resin ester from Hercules Corp as a tackifer and mineral oil as a plasticizer. The bioabsorbable adhesive layer is 4" by 4".

A 3" by 3" collagen matrix 61 is secured to the center of the bioabsorbable adhesive 64 layer so that a periphery of bioabsorbable adhesive comes in contact with the wound bed as illustrated in FIG. 6. The collagen matrix is of the type disclosed in parent applications Ser. Nos. 593,733; 843,828; and 875,827. The collagen matrix is made from purified Type I collagen derived from bovine tendon. The collagen matrix has an average pore size of 150 microns, with the collagen comprising about 2% by weight of the matrix. The fibers of the collagen matrix have a diameter of 10 microns. The matrix has a stiffness of $10^4$ Newtons/m$^2$. The collagen matrix absorbs twenty times its weight in liquid and allows both gas and moisture to freely permeate the matrix.

The collagen provides epithelial and fibroblast cells in the wound bed with a scaffold on which to attach themselves and grow. The combination of the increased migration activity provided by the collagen and the angiogenesis facilitated by the bioabsorbable adhesive makes this wound dressing effective in wound healing. In addition, after removal of the wound dressing, some of the collagen remains in the wound bed permanently which continues to aid healing.

E. The Release Layer

The fifth layer of the wound dressing illustrated in FIG. 6 was a release layer 65 comprised of polydimethylsiloxane, SCK-Silicone Coated Kraft from James River Paper Co. which is peeled away from the dressing before it is applied to the wound bed.

EXAMPLE 2

A. The Occlusive Outer Polymer Film Layer

The outer polymer film layer is the butyl acrylate, microporous polyether polyurethane described in Example 1(A).

B. The Adhesive Layer

The adhesive layer is the pressure sensitive butyl acrylate adhesive described in Example 1 (B) which is secured to the outer polymer layer as described in Example 1 (A).

C. The Inner Polymer Layer

The inner polymer layer is the microporous polyether polyurethane described in Example 1(A). The inner polymer layer is 4" by 4".

D. The Collagen Matrix Layer

A 3" by 3" collagen matrix of the type described in Example 1(A) is secured to the center of the inner polymer film layer.

E. The Bioabsorbable Adhesive

A coating of polyisobutylene bioabsorbable adhesive described in Example 1(D) approximately 1 ml thick is applied to the collagen matrix via spray drying.

F. The Release Layer

The release layer, the polydimethylsiloxane described in Example 1(E), is secured onto the bioabsorbable adhesive.

EXAMPLE 3

A. The Outer Polymer Layer

The outer polymer layer is a Teflon\membrane (W. L. Gore Assoc.) having a moisture vapor transmission rate of 500 gms/cm$^2$/per 24 hour period.

B. The Adhesive Layer

The second layer is a polyvinyl ether adhesive (a composition of a polyacrylamide adhesive with polyvinylether) which secures the outer polymer layer to the inner polymer layer.

C. The Inner Polymer Layer

The inner polymer layer, that closest to the collagen matrix, is the microporous polyether polyurethane described in Example 1(C).

D. The Collagen Matrix Layer

The collagen matrix of the type described in Example 1(D) is secured to the inner polymer layer as described in Example 2(D).

E. The Bioabsorbable Adhesive Layer

The bioabsorbable adhesive layer which is spray dried onto the collagen matrix secured to the center of the inner polymer layer is polyacrylamide (Model TT 5092-00 from Semex Medical) containing the hydrophils carboxymethyl cellulose (7 MXFCMC from Hercules Corp), starch-graft (a WaterLock Product from Grain Processing Corp.), pectin and gelatin utilizing a Piccotac\resin ester from Hercules Corp as a tackifier.

F. The Release Layer

The release layer of the wound dressing is the polydimethylsiloxane layer described in Example 2(F).

EXAMPLE 4

A further wound dressing of the type illustrated in FIG. 6 comprises:

A. The Outer Polymer Layer

The outer polymer layer 63a is the butyl acrylate/microporous polyether polyurethane described in Example 1(A).

B. The Adhesive

The adhesive 64 securing the polymer of (A) 63a to the polymer of (C) 63b is a water based urethane dispersion. The adhesive is secured to the polymer layers as described in Example 1(B).

C. The Inner Polymer Layer

The inner polymer layer 63b is a Teflon\membrane (from W. L. Gore Assoc.) having a moisture vapor transmission rate of from 5–10,000 gms/cm$^2$/24 hour period.

D. Bioabsorbable Adhesive - Collagen Matrix

The fourth layer is the bioabsorbable adhesive polyisobutylene containing hydrophils and tackifiers and collagen layer described in Example 1(D).

E. The Release Layer

The release layer 65 is the polydimethylsilxane described in Example 1(E).

What is claimed is:

1. A wound dressing to promote the progressive healing of a wound comprising:
   (a) a crosslinked collagen matrix;
   (b) a bioabsorbable adhesive coated on the surface of the collagen matrix to be placed in contact with the wound bed whereby the matrix affords epithelial and fibroblast cells in the bed with a scaffold on which to attach themselves and grow and the adhesive facilities wound healing; and
   (c) a multilayer polymer film secured to the opposite surface of the collagen matrix comprising a first layer having predetermined moisture and gas transmissivity characteristics appropriate to the wound to be healed superposed with the collagen matrix, and a second layer remote from the collagen matrix having relatively reduced moisture and gas transmissivity characteristics to render it more occlusive than the first layer to promote new cell growth in the early stages of wound healing, and strippable from the film after a period of time sufficient for the earlier stages of wound healing to take place to provide thereafter increased moisture vapor transmission between the wound bed and the atmosphere.

2. The wound dressing of claim 1, wherein the collagen matrix is formed from Type I or Type III collagen.

3. The wound dressing of claim 2, wherein the collagen matrix comprises fibers defining surface and interior pores connected by internal channels, the average pore size being from 50 to 350 microns and the collagen comprising from 2 to 30% by volume of the matrix.

4. The wound dressing of claim 1, wherein the bioabsorbable adhesive is a material selected from the group consisting of polyisobutylenes, acrylic emulsions, polyvinyl ethyl ethers admixed with hydrogenated resin esters, natural rubber latex, collagen adhesives, and water based urethane emulsions.

5. The wound dressing of claim 4, wherein the bioabsorbable adhesive is polyisobutylene containing polyacrylamides, carboxymethylcellulose, starch graft copolymers, pectins, gelatins, resin esters or hydrocarbons.

6. The wound dressing of claim 1, wherein the second polymer layer which is farthest away from the collagen matrix permits from 0 to 500 g/cm$^2$ per 24 hours moisture transmission and from 500 to 6000 cm$^3$ m$^2$-Atmos-24 hour oxygen permeation; whereas the first polymer layer closest to the collagen matrix permits from 500 to 5000 g/cm$^2$ per 24 hours moisture transmission and from 6000 to 20,000 cm$^3$-m$^2$ - Atmos-24 hours oxygen permeation.

7. The wound dressing of claim 1, wherein the first polymer layer which is farthest away from the collagen matrix comprises a polymer selected from the group consisting of microporous polyether polyurethanes, polyester polyurethanes, microporous polyvinyl chlorides, polyolefins, cellulose acetate, polydifluroethylene, ethylene vinyl acetate, ionomeric films, silicone latex, biodegradable urethanes and acrylics; whereas the first polymer layer closest to the collagen matrix comprises a polymer selected from the group consisting of microporous polyether polyurethanes, polyester polyurethanes, microporous polyvinylchlorides, polyolefins, cellulose acetate, polydifluoroethylene, ethylene vinyl acetate, ionomeric films, silicone latex, biodegradable urethanes and acrylics and polyisobutylenes.

8. The wound dressing of claim 1, wherein the multilayer polymer film extends beyond the periphery of the collagen matrix for securing the dressing to surrounding, non-injured skin.

* * * * *